United States Patent [19]

Michel et al.

[11] Patent Number: 4,824,965
[45] Date of Patent: Apr. 25, 1989

[54] 4-OXO-4,5,6,7-TETRAHYDROINDOLE DERIVATIVES

[75] Inventors: Helmut Michel, Mannheim; Roland Ofenloch, Lorsch, both of Fed. Rep. of Germany

[73] Assignee: Boehringer Mannheim GmbH, Mannheim, Fed. Rep. of Germany

[21] Appl. No.: 136,834

[22] Filed: Dec. 22, 1987

Related U.S. Application Data

[62] Division of Ser. No. 438,663, Nov. 2, 1982, Pat. No. 4,736,043.

[30] Foreign Application Priority Data

Nov. 28, 1981 [DE] Fed. Rep. of Germany ....... 3147276

[51] Int. Cl.⁴ .......................................... C07D 209/42
[52] U.S. Cl. .................................................. 548/492
[58] Field of Search ................................ 548/492, 516

[56] References Cited

U.S. PATENT DOCUMENTS 3,510,491 5/1970 Bell ..................................... 548/492
3,654,303 4/1972 Remers et al. ..................... 548/516

OTHER PUBLICATIONS

R. Marchelli et al., Can. J. Chem. 1969, 47(23), 4375–4381, Preparation and Properties of the Hydroxyindole-3-Carboxylic Acids.
R. Marchelli et al., Chem. Abstracts, vol. 72, No. 12470c (1969), Preparation and Properties of the Hydroxyindole-3-Carboxylic Acids.
S. Hauptmann et al., Chem. Abstracts, vol. 64, No. 17521h (1966), Hydroxyindoles 4-oxo-4,5,6,7-Tetrahydroindoles from Cyclohexanedione and Isonitroso Carbonyl Compounds.

Primary Examiner—Mary E. Ceperley
Attorney, Agent, or Firm—Felfe & Lynch

[57] ABSTRACT

The present invention provides a process for the preparation of 4-hydroxyindole derivatives of the general formula:

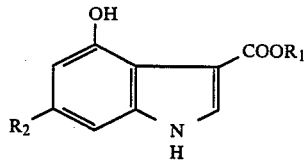

in which $R_1$ is a hydrogen atom or an alkyl radical containing up to 6 carbon atoms and $R_2$ is a hydrogen atom or an alkyl radical containing up to 6 carbon atoms, wherein a compound of the general formula:

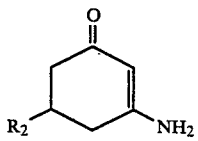

in which $R_2$ has the same meaning as above, is reacted with a compound of the general formula:

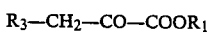

in which $R_1$ has the same meaning as above and $R_3$ is a reactive residue, to give a 2-(2-imino-6-oxocyclohexylidene)-propionic acid derivative of the general formula:

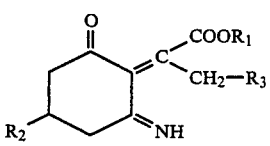

in which $R_1$, $R_2$ and $R_3$ have the same meanings as above, which is then cyclized in known manner to give a compound of the general formula:

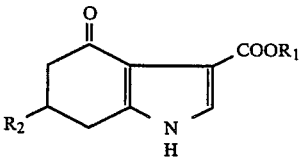

in which $R_1$ and $R_2$ have the same meanings as above, which is subsequently dehydrated.

The present invention also provides new 4-hydroxyindoles of the general formula (I'), as well as new 4-oxoindoles of general formula (IV).

3 Claims, No Drawings

4-OXO-4,5,6,7-TETRAHYDROINDOLE DERIVATIVES

This application is a divisional of Ser. No. 438,663, filed Nov. 2, 1982, now U.S. Pat. No. 4,736,043.

The present invention is concerned with a process for the preparation of indole derivatives, with the use thereof as intermediates and with new 4-hydroxyindoles and 4-oxoindoles.

The indole derivatives with which the present invention is concerned are compounds of the general formula:

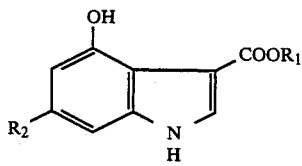

wherein $R_1$ is a hydrogen atom or an alkyl radical containing up to 6 carbon atoms and $R_2$ is a hydrogen atom or an alkyl radical containing up to 6 carbon atoms.

We have found that the new process according to the present invention gives, in a simple manner, valuable intermediates of great purity which are useful for the preparation of compounds with useful pharmaceutical properties, for example aminopropanols having β-blocking activity for useful combatting angina pectoris and other cardiac diseases.

Compounds of general formula (I), wherein $R_2$ is a hydrogen atom, are known from the literature and have already been prepared by a different process (see Can. J. Chem., 47, 4375/1969).

According to the above literature reference, 4-benzyloxyindole is converted into the magnesium compound, reacted with ethyl chloroformate, subjected to a chromatographic purification, which results in very considerable losses, and subsequently hydrogenolytically debenzylated. The 4-benzyloxyindole required as starting material must be prepared in a multi-step synthesis from a 1,2,3-trisubstituted benzene derivative.

According to the process of the present invention for the preparation of compounds of general formula (I), a compound of the general formula:

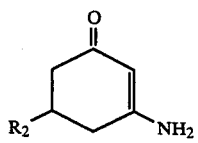

in which $R_2$ is a hydrogen atom or a lower alkyl radical, is reacted with a compound of the general formula:

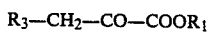

in which $R_1$ is a hydrogen atom or a lower alkyl radical and $R_3$ is a reactive residue, to give a compound of the general formula:

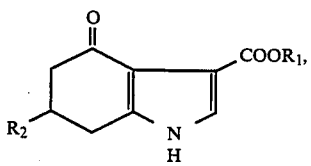

in which $R_1$, $R_2$ and $R_3$ have the same meanings as above, which is cyclised to give a compound of the general formula:

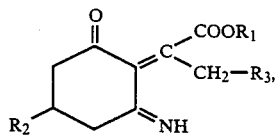

in which $R_1$ and $R_2$ have the same meanings as above, which is subsequently dehydrogenated in known manner to give the desired compound of general formula (I).

The lower alkyl radicals $R_1$ and $R_2$ can be straight-chained or branched and contain up to 6 carbon atoms, the methyl and ethyl radicals being preferred. The reactive residue $R_3$ is, in particular, a halogen atom, chlorine and bromine being preferred.

Compounds of general formula (IV), as well as those of general formula (I), in which $R_2$ is a lower alkyl radical, are new and also the subject of the present invention.

Compounds of general formula (I) can be further reacted by known methods, for example by saponification and decarboxylation to give 4-hydroxyindole or 4-hydroxy-6-methylindole, or by aminolysis and dehydration to give 4-hydroxy-3-cyanoindole or 4-hydroxy-3-cyano-6-methyl-indole, which, by reaction with epichlorohydrin and alkylamino derivatives, give aminopropanols with useful pharmacological properties (see Federal Republic of Germany Patent Specification Nos. 25 08 251; 27 37 630; 29 05 877 and 30 30 047). However, compounds of general formula (I) can also be reacted to give aminopropanol derivatives directly, whereafter the compounds obtained are subsequently changed. Thus, for example, from 4-hydroxy-3-cyanoindole (see Federal Republic of German Patent Specification No. 30 29 980) there is obtained 4-(2,3-epoxypropoxy)-3-cyanoindole which is reacted with 2-(2-allyloxyphenoxy)-ethylamine to give the pharmacologically effective 4-{2-hydroxy-3-[2-(2-allyloxyphenoxy)-ethylamino]-propoxy}-3-cyanoindole (see Example 3h) of Federal Republic of German Patent Specification No. 30 30 047).

Compounds of general formulae (II) and (III) are either known from the literature or can be obtained by generally known methods.

The dehydrogenation of compounds of general formula (IV) is carried out by conventional methods under a protective gas atmosphere, using a noble metal catalyst, especially palladium.

The following Examples are given for the purpose of illustrating the present invention:

EXAMPLE 1

Ethyl 3-bromo-2-(2-imino-5-oxocyclohexylidene)propionate 111.1 g. 1-Aminocyclohex-1-en-3-one (see Arch. Pharm., 294, 763/1961) are added at 30° C., with stirring, to 760 ml. ethyl bromopyruvate. The reaction mixture is then heated to 60° C. for 8 hours. After cooling, the reaction mixture is mixed with 200 ml. ethyl acetate and 1000 ml. diethyl ether and filtered with suction. After washing the solid product with diethyl ether, there are obtained 247 g. (85% of theory) ethyl 3-bromo-2-(2-imino-6-oxocyclohexylidene)-propionate; m.p. 170°–175° C.

In an analogous manner, there is obtained ethyl 3-bromo-2-(2-imino-4-methyl-6-oxocyclohexylidene)propionate from 1-amino-5-methylcyclohex-1-en-3-one and ethyl bromopyruvate; m.p. 165°–170° C. The yield is 92% of theory.

EXAMPLE 2

3-Ethoxycarbonyl-4,5,6,7-tetrahydro-4-oxoindole 131 g. Ammonium acetate and 139.5 g. anhydrous sodium acetate are suspended in 1 liter n-butanol and, while stirring, 247 g. ethyl 3-bromo-2-(2-imino-6-oxocyclohexylidene)-propionate are added thereto, whereafter the reaction mixture is heated under reflux for 6 hours. After cooling, the reaction mixture is poured into a solution of 143 g. sodium bicarbonate in 1 liter water and stirred overnight at ambient temperature. The organic phase is separated off, dried with anhydrous sodium sulphate and evaporated in a vacuum. After trituration of the residue with isopropanol, suction filtration and drying, there are obtained 86 g. (48% of theory) 3-ethoxycarbonyl-4,5,6,7-tetrahydro-4-oxoindole; m.p. 221°–223° C.

In an analogous manner, there is obtained 3-ethoxycarbonyl-4,5,6,7-tetrahydro-4-oxo-6-methylindole from ethyl 3-bromo-2-(2-imino-4-methyl-6-oxocyclohexylidene)-propionate, using ammonium acetate and sodium acetate; m.p. 198°–200° C.; the yield is 64% of theory.

EXAMPLE 3

3-Ethoxycarbonyl-4-hydroxyindole 86.6 g. 3-Ethoxycarbonyl-4,5,6,7-tetrahydro-4-oxoindole are heated under reflux for 20 hours in 1 liter diethylene glycol dimethyl ether in the presence of 50 g. 10% palladium-charcoal. After filtering off the catalyst with suction and evaporating the filtrate in a vacuum, the residue obtained is triturated with diethyl ether and filtered off with suction. There are obtained 78 g. (90% of theory) 3-ethoxycarbonyl-4-hydroxyindole; m.p. 151°–153° C.

In an analogous manner, there is obtained 3-ethoxycarbonyl-4-hydroxy-6-methylindole; m.p. 152°–154° C. The yield is 90% of theory.

EXAMPLE 4

4-Hydroxyindole 44 g. 3-Ethoxycarbonyl-4-hydroxyindole are heated under reflux for 1.5 hours with 19,2 g. sodium hydroxide in 400 ml. ethanol and 100 ml. water. The carboxylic acid obtained (m.p. 234°–236° C. (decomp.)) is boiled in 250 ml. quinaldine for 30 minutes with 1 g. copper powder. After working up in conventional manner, there is obtained 4-hydroxyindole; m.p. 97°–100° C.

EXAMPLE 5

4-Hydroxy-3-cyanoindole 5 g. 3-Ethoxycarbonyl-4-hydroxyindole are heated in an autoclave to 100° C. for 12 hours in 150 ml. methanol and 150 ml. liquid ammonia. The amide obtained is heated under reflux for 5 hours in 50 ml. acetic anhydride. After saponification of the O-acetyl compound thus obtained, there is obtained 4-hydroxy-3-cyanoindole; m.p. 206°–207° C.

It will be understood that the specification and examples are illustrative but not limitative of the present invention and that other embodiments within the spirit and scope of the invention will suggest themselves to those skilled in the art.

What is claimed is:

1. A 4-oxo-4,5,6,7-tetrahydroindole derivative of the general formula:

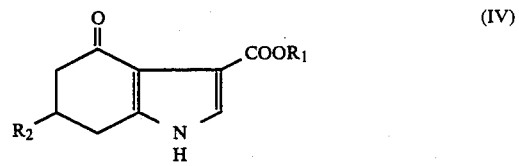

wherein $R_1$ is a hydrogen atom or an alkyl radical containing up to 6 carbon atoms and $R_2$ is a hydrogen atom or an alkyl radical containing up to 6 carbon atoms.

2. A 4-oxo-4,5,6,7-tetrahydroindole compound as claimed in claim 1 which is designated 3-ethoxycarbonyl-4,5,6,7-tetrahydro-4-oxo-6-methylindole.

3. A 4-oxo-4,5,6,7-tetrahydroindole compound as claimed in claim 1 which is designated 3-ethoxycarbonyl-4,5,6,7-tetrahydro-4-oxoindole.